United States Patent
Sander

(10) Patent No.: US 7,434,934 B2
(45) Date of Patent: Oct. 14, 2008

(54) EYE-PROTECTION APPARATUS, IN PARTICULAR RETINA-PROTECTION APPARATUS, AND OPTICAL ELEMENT HAVING A FREE-FORM SURFACE FOR AN ILLUMINATION BEAM PATH, AND USE OF AN OPTICAL ELEMENT HAVING A FREE-FORM SURFACE

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 282 days.

(21) Appl. No.: 11/148,765

(22) Filed: Jun. 9, 2005

(65) Prior Publication Data

US 2005/0283142 A1    Dec. 22, 2005

(30) Foreign Application Priority Data

Jun. 11, 2004    (DE)    ........................ 10 2004 028 470

(51) Int. Cl.
*A61B 3/10*    (2006.01)
(52) U.S. Cl. ...................................... 351/221; 351/216
(58) Field of Classification Search ................. 351/221; 359/672–675
See application file for complete search history.

(56) References Cited

U.S. PATENT DOCUMENTS

| 4,715,704 | A  |   | 12/1987 | Biber et al. |
|-----------|----|---|---------|--------------|
| 6,160,668 | A  | * | 12/2000 | Rogers ........................ 359/674 |
| 2003/0184881 | A1 | * | 10/2003 | Itonaga ........................ 359/719 |
| 2005/0057796 | A1 | * | 3/2005 | Shafer et al. ................. 359/357 |
| 2006/0171020 | A1 | * | 8/2006 | Krahmer et al. ............. 359/355 |
| 2007/0008490 | A1 | * | 1/2007 | Nagata et al. ................ 351/211 |

FOREIGN PATENT DOCUMENTS

| DE | 10207379 | 9/2003 |
|----|----------|--------|
| EP | 0611547  | 8/1994 |

* cited by examiner

*Primary Examiner*—Jordan M Schwartz
(74) *Attorney, Agent, or Firm*—Hodgson Russ LLP

(57) ABSTRACT

An eye-protection apparatus, in particular retina-protection apparatus, for a surgical microscope, having an illumination beam that defines an illuminated field for an object plane (14) and having an optical element (4) in the illumination beam path, wherein the optical element is embodied in such a way that it deflects light away from a central region or a decentral region of the illuminated field.

8 Claims, 4 Drawing Sheets

EYE-PROTECTION APPARATUS, IN PARTICULAR RETINA-PROTECTION APPARATUS, AND OPTICAL ELEMENT HAVING A FREE-FORM SURFACE FOR AN ILLUMINATION BEAM PATH, AND USE OF AN OPTICAL ELEMENT HAVING A FREE-FORM SURFACE

CROSS REFERENCE TO RELATED APPLICATIONS

This application claims priority of the German patent application 10 2004 028 470.9 filed Jun. 11, 2004 which is incorporated by reference herein.

FIELD OF THE INVENTION

The invention concerns an eye-protection apparatus, in particular a retina-protection apparatus, and an optical element having a free-form surface for an illumination beam path, as well as the use of an optical element having a free-form surface to protect the retina of the patient's eye in the course of eye surgery. The patient's eye needs to be protected at times from the light used by a surgeon to illuminate the surgical field on the eye. The retina, as well as the cornea and lens, could otherwise be damaged by an excessive radiation dose.

BACKGROUND OF THE INVENTION

Filters that filter out the damaging spectral portions of the light are usually used in surgical microscopes.

DE-A1-33 39 172 describes a light trap for surgical microscopes. Zones of the illuminated field in the object field are shadowed using a stop that can be pivoted into the illumination beam path of a surgical microscope. The shadowing of the center of the illuminated field in the region of the pupil prevents a damaging light beam from striking the retina of the patient's eye. A dark spot is therefore formed at the center of the illuminated field above the patient's pupil.

The disadvantage here, however, is that this absorption of light by the stop in the center of the illumination beam path results in waste heat, so that, for example, the support material might crack. In addition, a not inconsiderable portion of the light is lost as a result of the light-absorbing coating of the stop.

SUMMARY OF THE INVENTION

The object therefore arises of discovering a protective apparatus of the species that does not cause any waste heat to be produced. The inventor achieves this object by an eye-protection apparatus, for a surgical microscope, comprising an illumination beam that defines an illuminated field for an object plane, and an optical element positioned in the illumination beam path, wherein the optical element is embodied in such a way that it deflects light away from a central region or a decentral region of the illuminated field.

The object therefore arises of discovering an optical element of the species that does not cause any waste heat to be produced. The inventor achieves this object by way of an optical element comprising a free-form surface, wherein the optical element is positioned in a path of an illumination beam that defines an illuminated field, and in use the optical element deflects light away from a central region or a decentral region of the illuminated field into a remaining region of the same illuminated field.

The eye-protection apparatus, in particular retina-protection apparatus, according to the present invention for a surgical microscope comprises a means for generating an illumination beam that defines an illuminated field of an object plane, as well as an optical element in the illumination beam path which is embodied in such a way that it deflects light away from a central region of the illuminated field. In a particular case in which the eye is rolled away and the pupil is not located in the central region, the light is deflected away from a decentral region of the illuminated field corresponding to that position. With this apparatus, the light is not converted into heat at the central region or at the decentral region, but instead is directed away from it. In a particular embodiment, either the intensity in the remaining region of the illumination beam path is increased, or light is directed into other lateral regions of the illumination beam that are unproblematic for the retina, the overall result being to generate less waste heat than the absorption described in DE-A1-33 39 172. The shape of the resulting shadow in the illuminated field can be congruent with the optical element, but can also assume any other conceivable shape.

An optical element of this kind can partially exhibit an infinite radius in its peripheral region, so that the deflection effect is absent there.

According to the present invention, in accordance with one embodiment the surface of the optical element is constituted by a free-form surface. This free-form surface can also exhibit non-rotationally-symmetrical deviations from the spherical, preferably a topography that, for example, is represented by a higher-order polynomial (preferably 5th-order or higher).

With optical elements shaped in this fashion it is therefore possible for light to be deflected in the desired directions to the side of the central or decentral region. It is preferable to use in the microscope illumination system an optical element having a free-form surface instead of the previous retina protection stop, which surface is arranged in the central region or a decentral region of the illumination beam path in a plane conjugated with the object plane.

As a further embodiment, a surface of the condenser lenses or of another lens can likewise be configured as a free-form surface in order to achieve a comparable effect. An additional component can thus be dispensed with. The optical element can be selectably pivoted in and out of the illumination beam path in motorized and electrically or electronically controlled fashion, if applicable by remote control.

The eye-protection apparatus, in particular retina-protection apparatus, according to the present invention need not be used exclusively for a surgical microscope, but can also be incorporated into other optical devices.

Further embodiments of the invention are depicted in the Figures and described in the specification.

BRIEF DESCRIPTION OF THE DRAWINGS

The invention will be explained further, in symbolic and exemplifying fashion, with reference to the Figures, in which.

DETAILED DESCRIPTION OF THE INVENTION

Figure 1:
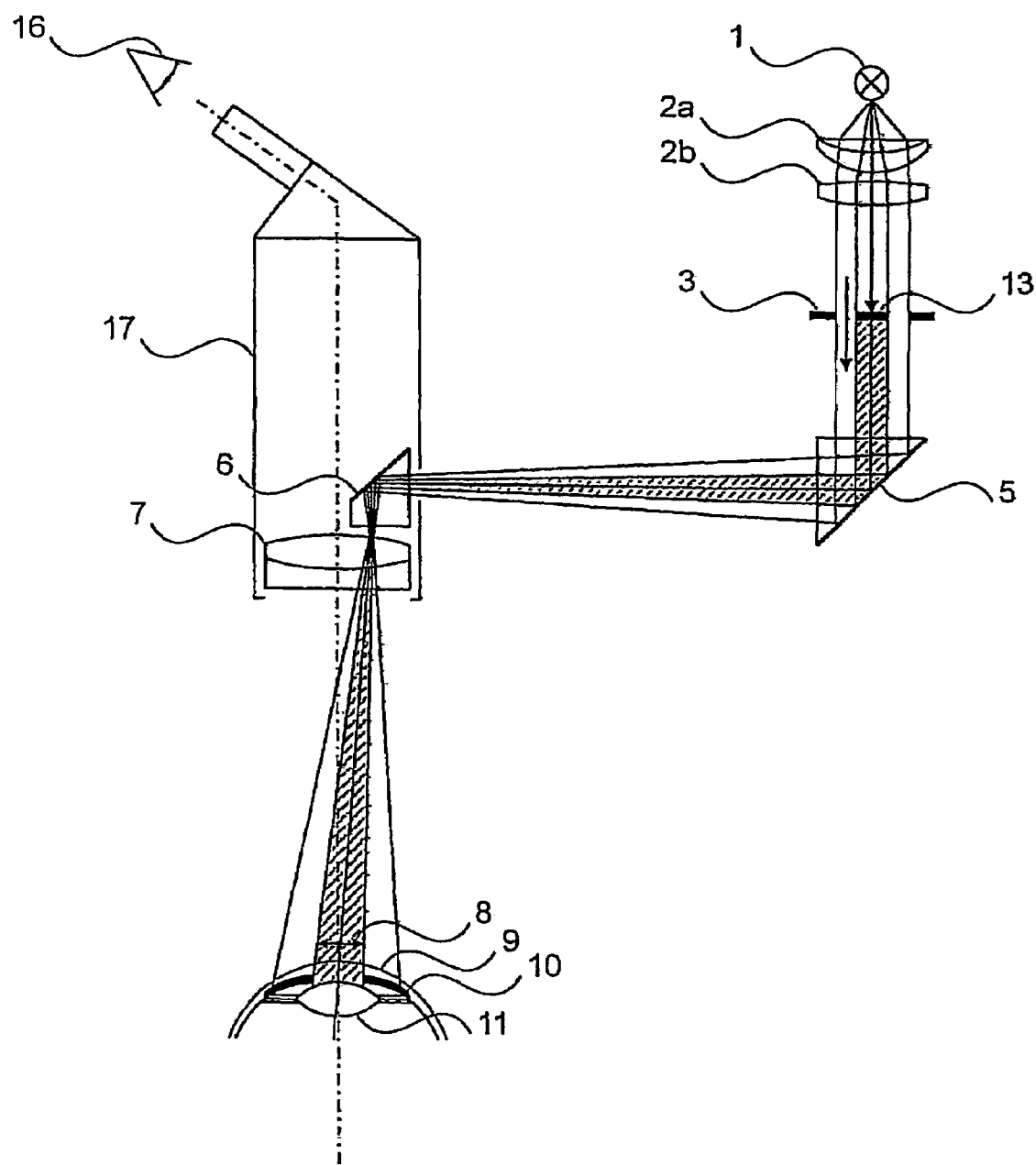
FIG. 1 schematically depicts an illumination beam path in an application of a retina protection stop according to the existing art.

FIG. 1 depicts an illumination beam path of a microscope 17 in an application of a retina protection stop 13 according to the existing art. Light is emitted from a light source 1 into the illumination beam path, which also comprises condenser lenses 2a and 2b in the illumination beam path, thereby providing an illumination beam. A field diaphragm 3 is located in a plane conjugated with the object plane, and a retina protection stop 13 that absorbs light in the central region of the illumination beam is located in the same plane. The remaining light arrives at the surgical field by way of deflection elements 5 and 6 and an optic 7. Shadow 8 generated by retina protection stop 13 covers the pupil in iris 10 of a patient's eye. The light may therefore possibly strike iris 10 through portions of cornea 9, but does not strike the pupil or lens 11 of the patient's eye, and therefore also not the retina of that eye. Observer's eye 16 of a surgeon is also depicted.

Figure 2:
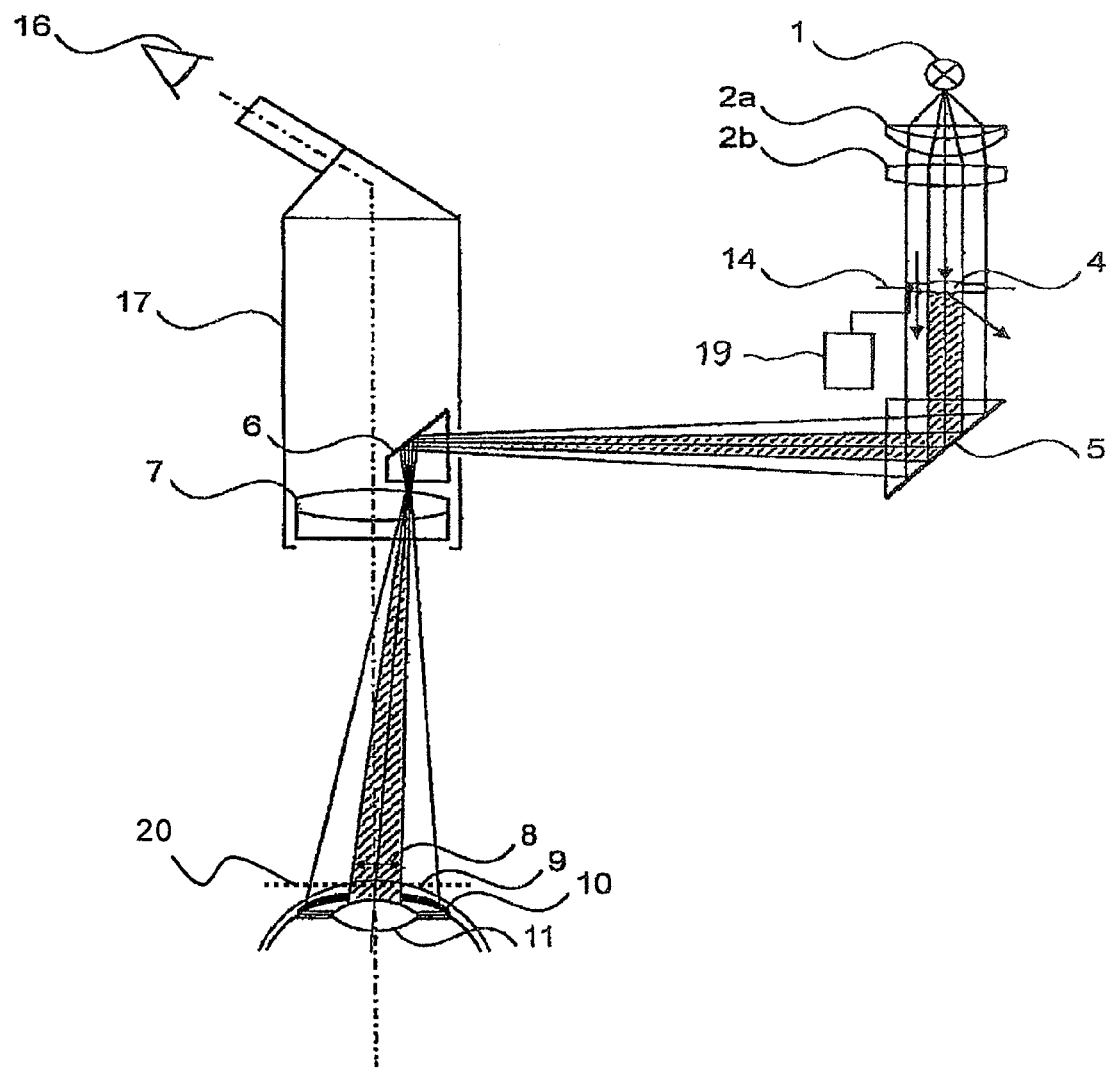
FIG. 2 schematically depicts an illumination beam path in an application of an optical element according to the present invention, in particular a special retina protection lens having a free-form surface.

FIG. 2 depicts the illumination beam path of a microscope 17 in an application of an optical element 4 according to the present invention, in particular a special retina protection lens having a free-form surface. Located in the plane 14 conjugate to the object plane 20 is optical element 4, in particular the retina protection lens, which deflects light out of the central region of the illumination beam rather than absorbing it. The light either increases the light intensity in the remaining region or is deflected into other lateral regions of the illumination beam that are unproblematic for the retina. Shadow 8 that is generated by the free-form surface of the retina protection lens produces the effect explained in the description of FIG. 1. Preferably, the optical element 4 can be selectably moved into and out of the illumination beam path by operation of an electric motor 19 connected to the optical element.

Figure 3:
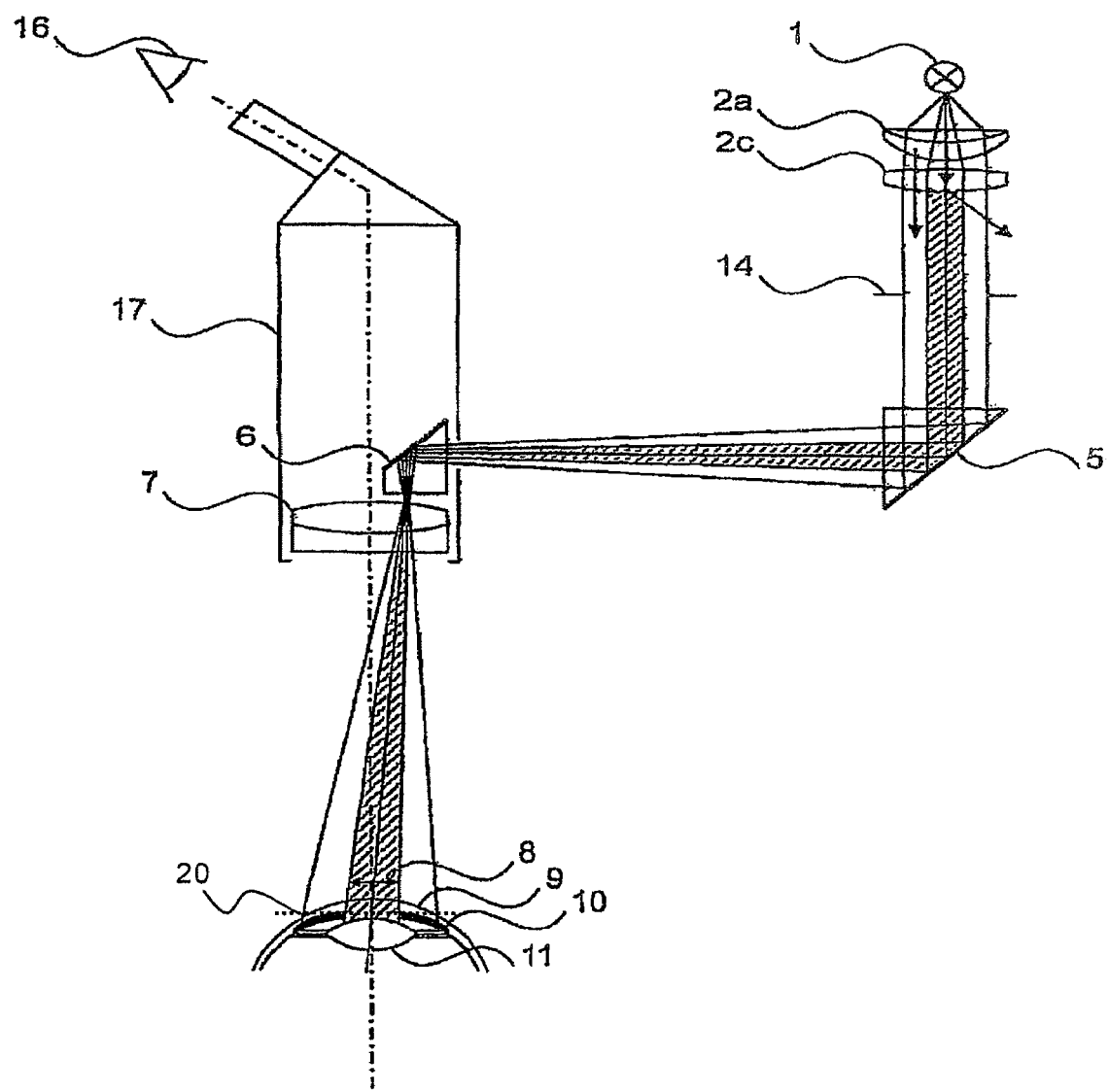
FIG. 3 schematically depicts an illumination beam path in an application of an optical element according to the present invention, in particular a condenser lens having a free-form surface.

FIG. 3 depicts the illumination beam path of a microscope 17 in an application of an optical element according to the present invention, in particular a condenser lens 2c having a free-form surface. Located outside the plane 14 conjugate to the object plane 20 is a condenser lens 2c having a free-form surface, which deflects light out of the central region of the illumination beam. Shadow 8 that is generated by the free-form surface of condenser lens 2c produces the effect explained in the description of FIG. 1.

Figure 4:
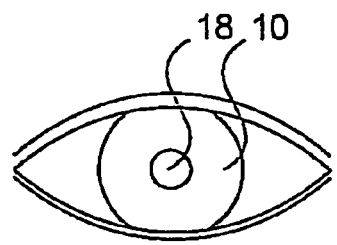
FIG. 4 schematically depicts a patient's eye in two different pupil positions.
Figure 4:
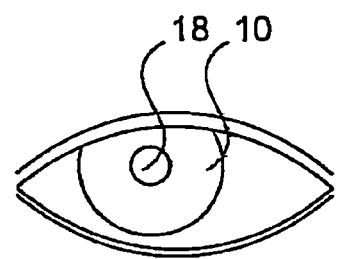

FIG. 4 depicts a patient's eye in two different pupil positions. In the upper part iris 10 with pupil 18 is oriented centrally, and in the lower part it is rolled toward the top left, i.e. oriented decentrally.

Figure 5:
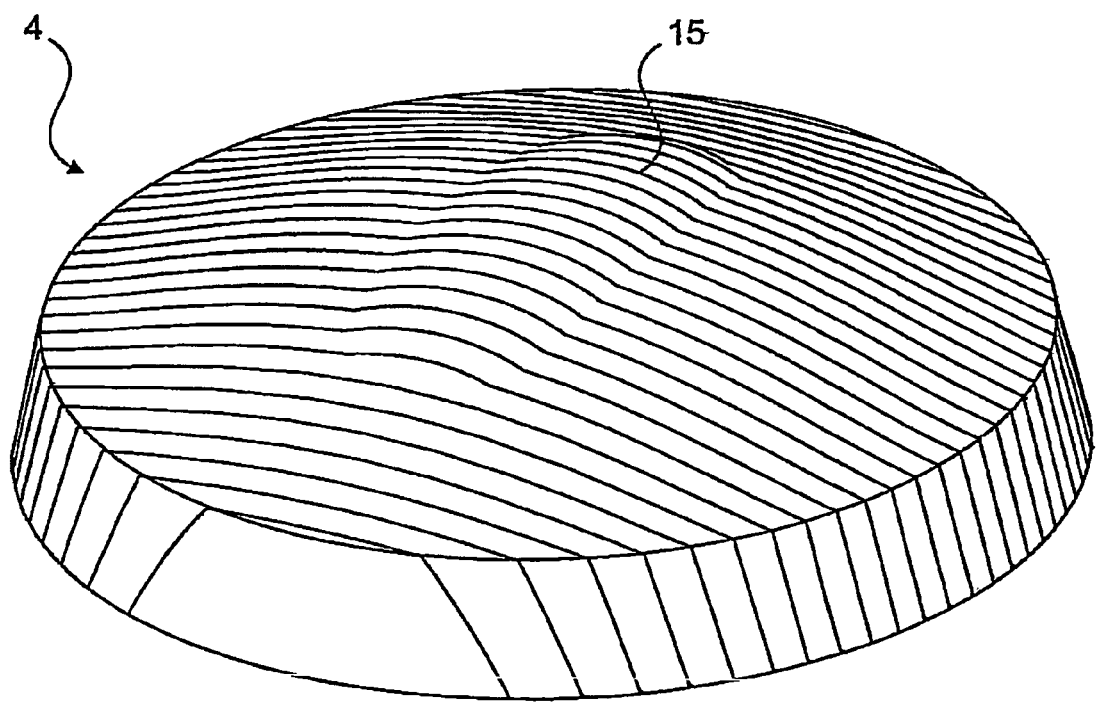
FIG. 5 schematically depicts an optical element according to the present invention, in particular a retina protection lens having a free-form surface.

FIG. 5 is an enlarged depiction of an optical element 4 according to the present invention, in particular a retina protection lens. Free-form surface 15 depicted by way of example is configured so that it deflects light away from the central region of the illuminated field.

What is claimed is:

1. An apparatus comprising:
   means for generating an illumination beam, the illumination beam defining an illuminated field of an object plane for illuminating in use a patient's eye positioned in the object plane, the illuminated field having a central region congruent with a centrally oriented position of the patient's eye and a decentral region congruent with a decentrally oriented position of the patient's eye; and
   an optical lens positioned in a path of the illumination beam deflecting light away from the central region or the decentral region of the illuminated field, wherein the optical lens generates a shadow covering the pupil in the iris of the patient's eye illuminated by the illumination field whether the pupil is located centrally or decentrally.

2. The apparatus as defined in claim 1, wherein the optical lens comprises at least one free-form surface.

3. The apparatus as defined in claim 2, wherein the at least one free-form surface is surrounded by a light transmissive surface exhibiting an infinite radius.

4. The apparatus as defined in claim 1, wherein the optical lens is arranged in a plane conjugate to the object plane.

5. The apparatus as defined in claim 1, wherein the optical lens comprises at least one condenser lens, on which condenser lens at least one free-form surface is configured.

6. The apparatus as defined in claim 1, wherein the optical lens is removable from the path of the illumination beam.

7. The apparatus as defined in claim 6, further comprising an electric motor connected to the optical lens, wherein the optical lens is removed from and inserted into the path of the illumination beam by operation of the electric motor.

8. The apparatus as defined in claim 2, wherein the light deflected away from the central region or the decentral region of the illuminated field is deflected into another region of the illuminated field.

* * * * *